United States Patent
Tsukerman (10) Patent No.: US 8,455,834 B2
(45) Date of Patent: Jun. 4, 2013

(54) SYSTEMS AND METHODS FOR PATIENT POSITIONING FOR NUCLEAR MEDICINE IMAGING

(75) Inventor: Leonid Tsukerman, Q. Mozkin (IL)

(73) Assignee: General Electric Company, Schenectady, NY (US)

( * ) Notice: Subject to any disclaimer, the term of this patent is extended or adjusted under 35 U.S.C. 154(b) by 794 days.

(21) Appl. No.: 12/629,533

(22) Filed: Dec. 2, 2009

(65) Prior Publication Data

US 2011/0129132 A1  Jun. 2, 2011

(51) Int. Cl.
*G01T 1/166* (2006.01)
*G21H 5/02* (2006.01)

(52) U.S. Cl.
USPC ............... 250/363.04; 250/363.03; 250/303

(58) Field of Classification Search
USPC ............ 250/363.02–363.04, 287; 382/128, 382/131
See application file for complete search history.

(56) References Cited

U.S. PATENT DOCUMENTS

| | | | |
|---|---|---|---|
| 3,904,530 A * | 9/1975 | Martone et al. .............. 250/369 | |
| 4,055,766 A | 10/1977 | Miller et al. | |
| 4,061,919 A | 12/1977 | Miller et al. | |
| RE30,904 E | 4/1982 | Miller et al. | |
| 5,249,124 A * | 9/1993 | DeVito ................. 250/363.04 | |
| 5,381,791 A * | 1/1995 | Qian ............................ 600/436 | |
| 5,462,056 A * | 10/1995 | Hawman et al. ............. 600/436 | |
| 5,871,013 A * | 2/1999 | Wainer et al. ................ 600/407 | |
| 5,936,248 A * | 8/1999 | Heukensfeldt Jansen ................ 250/363.07 | |
| 6,577,890 B1 | 6/2003 | Hayes et al. | |
| 6,782,071 B1 * | 8/2004 | Tsuyuki ............................ 378/4 | |
| 6,906,328 B2 | 6/2005 | Garrard et al. | |
| 7,127,826 B2 | 10/2006 | Russell | |
| 7,574,251 B2 | 8/2009 | Lu et al. | |
| 2006/0079759 A1 | 4/2006 | Vaillant et al. | |
| 2007/0081712 A1 | 4/2007 | Huang et al. | |
| 2007/0183642 A1* | 8/2007 | Ye et al. ..................... 382/131 | |
| 2008/0230703 A1* | 9/2008 | Kadrmas et al. ......... 250/363.03 | |
| 2008/0272304 A1* | 11/2008 | Vija ............................. 250/369 | |
| 2008/0300481 A1 | 12/2008 | Groszmann | |
| 2009/0088629 A1 | 4/2009 | Groszmann et al. | |
| 2009/0171183 A1 | 7/2009 | Narayanan et al. | |

* cited by examiner

*Primary Examiner* — Alexander H Taningco
(74) *Attorney, Agent, or Firm* — The Small Patent Law Group; Dean D. Small (57) ABSTRACT

Systems and methods for nuclear medicine (NM) imaging using different radiopharmaceuticals are provided. One method includes generating images of a region of interest (ROI) from radioactive emissions from a localization radiopharmaceutical to position the ROI in a field-of-view (FOV) of a gamma camera based on the generated images of the ROI. The method further includes performing an imaging scan of the ROI using an imaging radiopharmaceutical to acquire image data of the ROI, wherein the imaging radiopharmaceutical is different than the localization radiopharmaceutical.

26 Claims, 4 Drawing Sheets

SYSTEMS AND METHODS FOR PATIENT POSITIONING FOR NUCLEAR MEDICINE IMAGING

BACKGROUND OF THE INVENTION

The subject matter disclosed herein relates generally to nuclear medicine (NM) imaging systems, and more particularly to systems and methods for patient positioning to perform scans with NM imaging systems.

NM imaging systems, for example, Single Photon Emission Computed Tomography (SPECT) and Positron Emission Tomography (PET) imaging systems, use one or more image detectors to acquire imaging data, such as gamma ray or photon imaging data. The image detectors may be gamma cameras that acquire two-dimensional views of three-dimensional distributions of emitted radionuclides (from an injected radioisotope) from a patient being imaged.

In order to acquire NM imaging information for a region of interest (ROI), the ROI, such as a heart of a patient, must be positioned within a field-of-view (FOV) of the gamma camera. For example, in non-dynamic SPECT studies, such as myocardial perfusion imaging, the patient is positioned after the radiopharmaceutical is distributed in the patient body and uptakes into the patient's heart. Even though doctors know the general location of a patient's organ, differences in patient size, individual patient variability, organ size, etc. can lead to differences in the exact location of an organ. With gamma cameras having a smaller FOV, the patient may have to be moved back and forth multiple times to properly position the heart in the FOV. This back and forth process is time consuming and can increase the anxiety level of the patient.

Moreover, in dynamic studies, such as first-pass analysis and blood flow studies, among others, the ROI, such as the organ of interest is positioned prior to administration of the radiopharmaceutical. The positioning of the ROI can be difficult, and in some cases of dynamic imaging, may be almost impossible, such as trying to place the myocardium inside a smaller FOV of a gamma camera, because the radiopharmaceutical is not yet in uptake. Small FOV gamma cameras include, for example, gamma cameras with solid state detectors, or cameras fitted with fan beam, cone beam or pinhole collimators or may be dedicated cameras, such as for cardiac imaging, and have a smaller FOV.

BRIEF DESCRIPTION OF THE INVENTION

In accordance with various embodiments, a method for nuclear medicine (NM) imaging is provided. The method includes generating images of a region of interest (ROI) from radioactive emissions from a localization radiopharmaceutical to position the ROI in a field-of-view (FOV) of a gamma camera based on the generated images of the ROI. The method further includes performing an imaging scan of the ROI using an imaging radiopharmaceutical to acquire image data of the ROI, wherein the imaging radiopharmaceutical is different than the localization radiopharmaceutical.

In accordance with other embodiments, a method for nuclear medicine (NM) imaging is provided. The method includes performing a localization radiopharmaceutical study using a localization radiopharmaceutical to position a region of interest (ROI) of a patient in a field-of-view (FOV) of a gamma camera. The method further includes performing a dynamic radiopharmaceutical study using a dynamic radiopharmaceutical to acquire radiopharmaceutical uptake and redistribution information for the ROI, wherein the localization radiopharmaceutical is different than the dynamic radiopharmaceutical.

In accordance with yet other embodiments, a nuclear medicine (NM) imaging system is provided that includes an NM imaging scanner having at least one small field-of-view (FOV) imaging detector and a patient table supporting a patient thereon and positionable within the NM imaging scanner. The NM imaging system further includes a processor configured to acquire images of a region of interest (ROI) of the patient based on radioactive emissions from a localization radiopharmaceutical administered to the patient. The patient is positioned with the FOV of the gamma camera based on the acquired images. The processor is further configured to acquire dynamic NM image data of the positioned patient using an imaging radiopharmaceutical, wherein the localization radiopharmaceutical is different than the imaging radiopharmaceutical.

DETAILED DESCRIPTION OF THE INVENTION

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide systems and methods for positioning a region of interest (ROI) in a field-of-view (FOV) of a gamma camera, such as a gamma camera with a smaller or focused FOV. In various embodiments, patient positioning is implemented during a persistence imaging phase prior to administering the radiopharmaceutical for diagnostic imaging, such as for a dynamic nuclear medicine (NM) imaging. The locating and positioning of the ROI in the FOV of the gamma camera is accomplished using a localization radiopharmaceutical administered to a patient prior to the diagnostic study, and which uptakes into the ROI, for example, an organ such as the heart, prior to the start of the diagnostic study. The localization radiopharmaceutical used for the persistence phase of imaging the ROI in accordance with various embodiments has energy peaks that are non-overlapping with the main energy peaks of the radiopharmaceutical used for the diagnostic NM study. In accordance with various embodiments, the localization radiopharmaceutical is used as a marker for positioning the patient prior to a dynamic NM study.

A technical effect of at least some embodiments is enabling dynamic imaging in smaller FOV gamma cameras. Initial positioning of the ROI in the smaller FOV gamma camera also results in a reduced number of rescans or shorter scans as a result of proper positioning of the patient.

Figure 1:
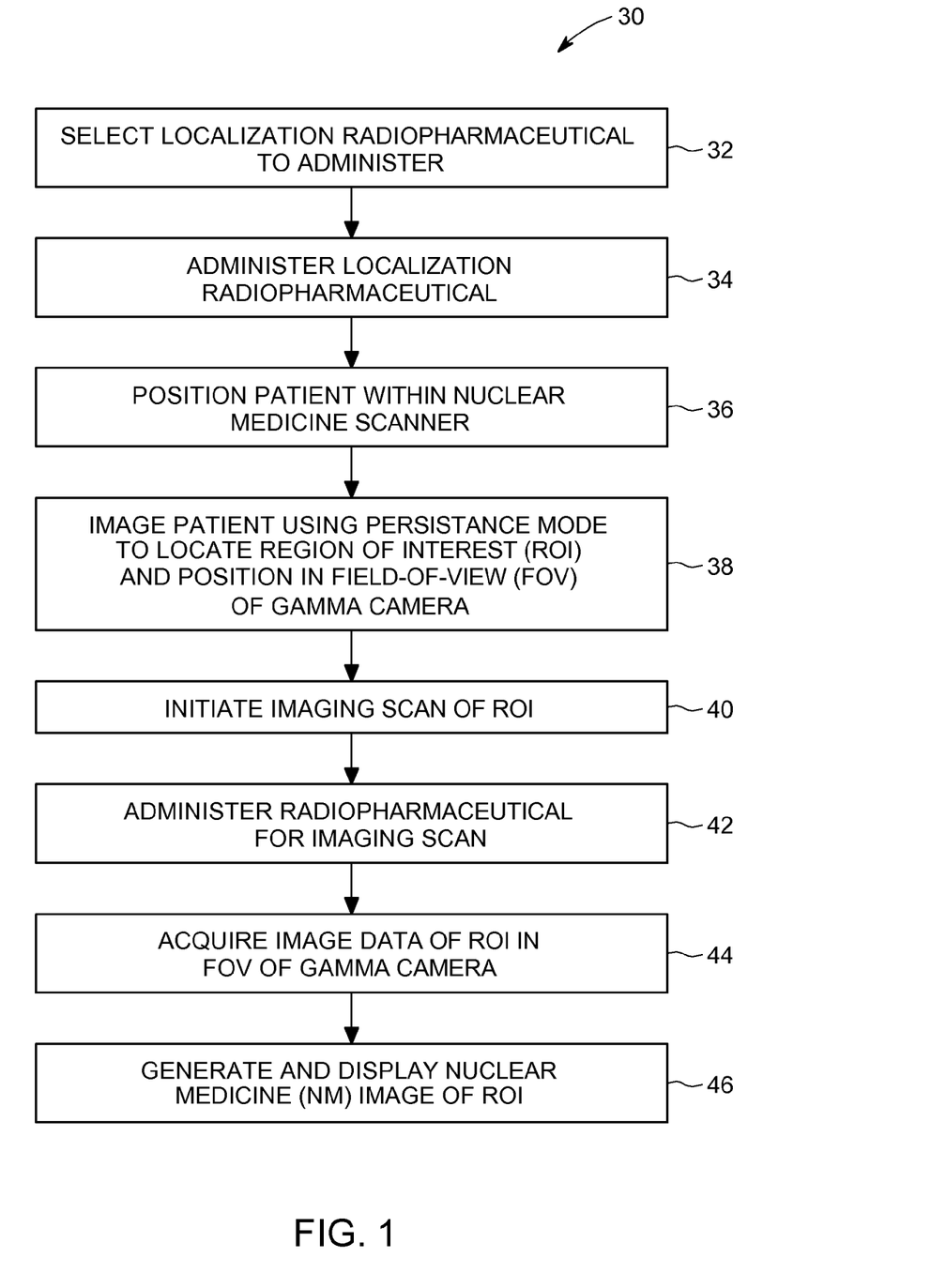
FIG. 1 is a flowchart of a method for performing a nuclear medicine (NM) study in accordance with various embodiments.

Specifically, various embodiments provide a method 30 as illustrated in FIG. 1 for performing an NM scan or study, for example, a dynamic NM study using a gamma camera having a small FOV. An NM study generally refers to acquiring NM data using one or more NM scans. The gamma camera may be different types of gamma detectors and have different types of collimators that create the small FOV. In various embodiments, the gamma camera includes focused collimators, such as pinhole collimators that focus on an ROI, such as focused on a patient's heart as described in more detail below.

The method 30 of FIG. 1 includes selecting a localization radiopharmaceutical to administer to a patient at 32. In the various embodiments, the selection of the localization radiopharmaceutical and/or the amount administered is based on the radiopharmaceutical that is to be used for a subsequent imaging scan after the patient is positioned using information acquired from the localization radiopharmaceutical. For example, the localization radiopharmaceutical is a different type of radiopharmaceutical than the radiopharmaceutical to be used subsequently for the NM imaging scan or study. In some embodiments, the localization radiopharmaceutical is selected such that the energy peak(s) for the localization radiopharmaceutical are different than the energy peak(s) for the radiopharmaceutical to be used for later diagnostic imaging. For example, in various embodiments the localization radiopharmaceutical is selected such that the energy peak(s) of the localization radiopharmaceutical do not overlap with the main energy peak(s) of the radiopharmaceutical used for the later diagnostic imaging. In some embodiments, the isotope used as the localization radiopharmaceutical has a lower energy window (including the energy peak) than the energy window of the isotope of the radiopharmaceutical used for the later diagnostic imaging. For example, the lower energy window of the localization radiopharmaceutical may be selected to reduce the likelihood or avoid scatter into the energy window of the radiopharmaceutical for diagnostic imaging.

The energy peak generally refers to the maximum energy emission from the decay of a radiopharmaceutical injected within a patient. The energy window generally refers to the energy used for image reconstruction, such as the photons with measured energy that fall within the energy range (defined by a width of an energy window) around the energy of the spectrum peak, which corresponds to the energy of the radioisotope as measured by a gamma camera.

Additionally, the dose for the localization radiopharmaceutical may be less than the dose for the radiopharmaceutical to be used for the diagnostic imaging. For example, the dose of the localization radiopharmaceutical may be a percentage amount less, such as 50% or 25% of the dose for the radiopharmaceutical to be used for the diagnostic imaging. In general, the localization radiopharmaceutical dose does not have to generate a clinical image for diagnosis, but provide images to locate the ROI, such as the organ of interest.

It should be noted that any type of radiopharmaceutical may be used as the localization radiopharmaceutical and may be based, for example, on the type of imaging scan to be performed subsequent to patient positioning using the localization radiopharmaceutical. Also, the imaging radiopharmaceutical as described in more detail below may be any type of radiopharmaceutical. For example, the radiopharmaceuticals that may be used in accordance with various embodiments (administered intravenously) include: Technetium-99m (technetium-99m), Iodine-123 and 131, Thallium-201, Gallium-67, Fluorine-18 Fluorodeoxyglucose and Indium-111 Labeled Leukocytes.

Other examples of the radiopharmaceuticals that may be used in accordance with various embodiments (administered in gaseous form) include: Xenon-133, Krypton-81m, Technetium-99m Technegas and Technetium-99m DTPA.

It should be noted that the localization radiopharmaceutical may also be used for purposes other than patient positioning. For example, the localization radiopharmaceutical may be selected to provide additional clinically relevant information, such as to perform a viability study to determine if heart tissue is alive. Accordingly, the localization radiopharmaceutical may provide clinical knowledge in addition to information (e.g., images) for patient positioning.

After the localization radiopharmaceutical is selected, the localization radiopharmaceutical is administered to a patient at 34. The administration of the localization radiopharmaceutical may be performed in any suitable manner, which may be based on the type of radiopharmaceutical selected (e.g., intravenous versus gaseous). In general, the localization radiopharmaceutical dose is administered internally (e.g. intravenous or orally). The localization radiopharmaceutical then uptakes into the patient's body, and in particular, the ROI. The localization radiopharmaceutical is produced to localize, for example, in an organ or body structure of interest. The localization radiopharmaceuticals may be formed from radionuclides that are combined with other chemical compounds or pharmaceuticals. The radiopharmaceutical, once administered to the patient, thus, localizes to specific organs or cellular receptors.

After the localization radiopharmaceutical uptakes and localizes in the organ of interest, radioactive emissions from the localization radiopharmaceutical, which uses one or more radioactive isotopes (radionuclides), are used to position the patient within the NM scanner, which first includes at 36 moving the patient into an opening of the NM scanner, which may be performed automatically, based on user input, or a combination thereof. Thereafter, using a persistence mode of imaging (also referred to as the persistence imaging phase), the patient is moved into position within the NM scanner to locate the ROI within the FOV of the gamma camera at 38. In general, a position within the FOV of the gamma camera for imaging the ROI is determined as described in more detail herein using generated images from the localization radiopharmaceutical.

Figure 2:
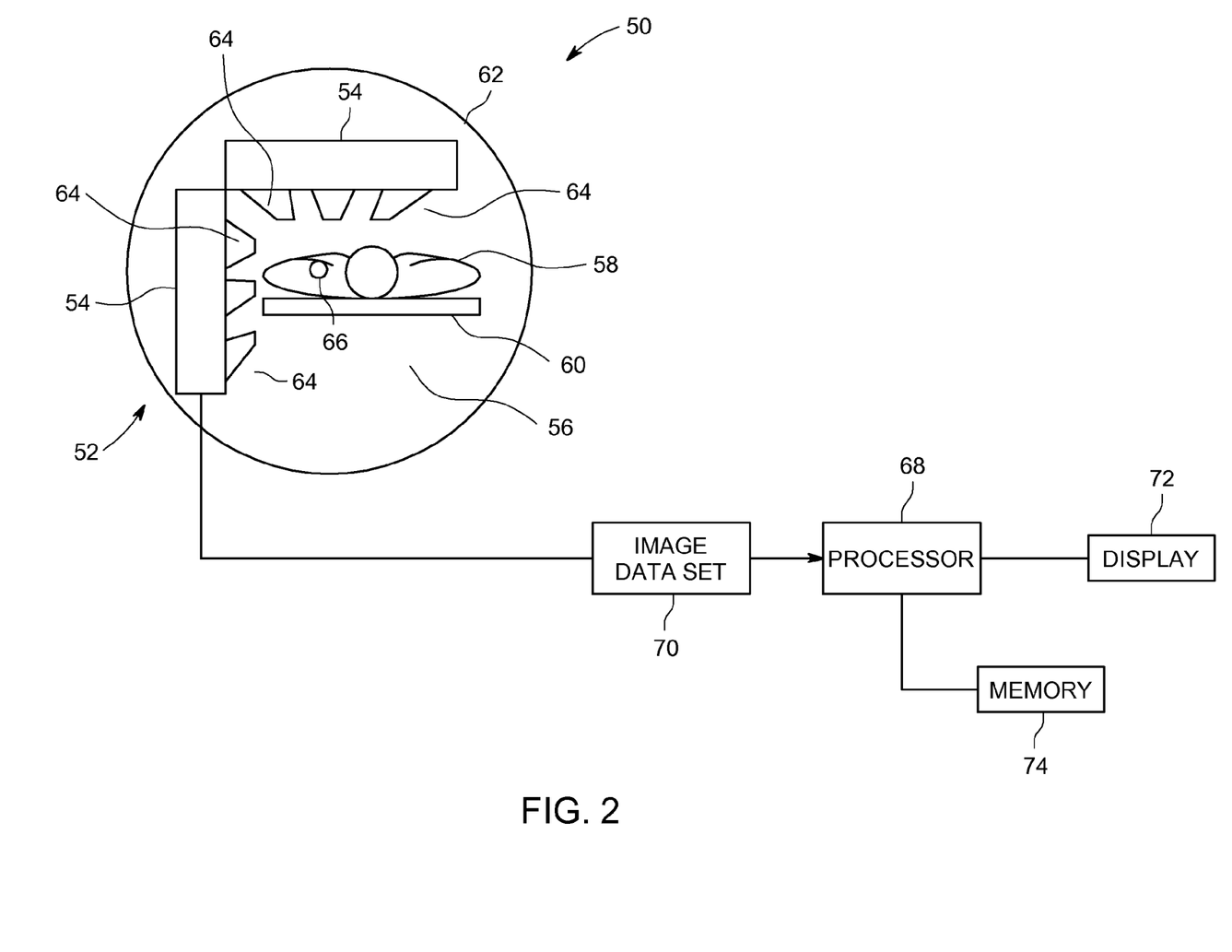
FIG. 2 is a diagram illustrating an NM imaging system in which various embodiments may be implemented.

The various embodiments may be implemented in connection with an imaging system 50 as shown in FIG. 2. The imaging system 50 is embodied as a NM imaging system, such as a single photon emission computed tomography (SPECT) or positron emission tomography (PET) imaging system. The imaging system 50 includes an NM scanner 52 including one or more detectors, such as a pair of detectors 54 (e.g., gamma detectors or gamma cameras) having a central opening 56 therethrough. The opening 56 is configured to receive an object therein, such as a patient 58 supported on a patient table 60. The detectors 54 are shown in an "L" mode configuration, but may be moved and positioned in other configurations such as an "H" mode configuration. Additionally, a gantry 62 may be configured in different shapes, for example, as a "C", "H" or "L". It should be noted that more or less detectors 54 may be provided.

The detectors 54 are supported on the gantry 62 to acquire NM data, such as emission photon data. The detectors 54 may be formed from different materials, such as cadmium zinc telluride (CdZnTe), often referred to as CZT, cadmium telluride (CdTe), and silicon (Si), among others, or from Sodium Iodide (Nap and used in combination with photomultiplier (PMT) tubes (not shown) as is known. In some embodiments, the detectors may be formed from a plurality of detector modules, each having a plurality of pixels. One or more collimators 64 may be provided in combination with the detectors 54 (or modules thereof), for example, to provide focused collimation toward a ROI 66 (illustrated as a heart) of the patient 58. Thus, the actual FOV for each of the detectors 54 (or portions thereof) may be decreased by the type of collimator, such as pinhole (or multi-pinhole) or converging collimator, thus forming gamma cameras with smaller or small FOVs. However, the smaller FOV gamma camera may be formed using any type of collimator that reduces the actual FOV of the detectors 54. Additionally, the actual FOV may be increased or remain relatively unchanged depending on the type of collimator 64 used. Additional examples of types of collimators 64 include parallel-beam converging, diverging fan-beam, converging or diverging cone-beam, multi-bore, multi-bore converging, multi-bore converging fan-beam, multi-bore converging cone-beam, multi-bore diverging, or other types of collimators.

The imaging system 50 also includes a processor 68 (e.g., workstation) that is coupled to the imaging system 50. During operation, the output from the detectors 54, which may be one or more image data sets 70 (or other image information), is transmitted to the processor 68 for processing, such as image reconstruction to form an image for display on a display 72.

Thus, for example, event count information, such as photon count information from the emissions of the radiopharmaceutical in the region of interest 66 (e.g., heart) of the patient 58 is obtained from the detectors 54. As shown in FIG. 2, the image data set 70, which may include raw image data for acquired by the detectors 52, may be reconstructed into a plurality of images for display on the display 72. For example, SPECT images of a heart may be displayed.

It should be noted that the raw data, such as the image data sets 70, may be stored for a short term (e.g., during processing) or for a long term (e.g., for later offline retrieval) in a memory 74. The memory 74 may be any type of data storage device, which may also store databases of information. The memory 74 may be separate from or form part of the processor 68.

Thus, for example, using a persistence mode image displayed on the display 72, which image is a real-time image (often of lower image resolution while the scan is being performed), the ROI 66 may be located and localized by moving the patient 58 into the opening 56 by moving the patient table 60, such as forward-backwards, up-down and left-right. Using the persistence image generated from image information from the decay of the localization radiopharmaceutical, the ROI 66 can be placed within the FOVs of the collimators 64, such that the detectors 52 are focused on the ROI 66 for diagnostic imaging as described below. For example, the patient 58 may be moved while viewing the image of the ROI 66 to position the ROI 66 in the center of the display 72, which may be indicated by a marking (e.g., a cross-mark). It should be noted that the persistence mode image is generally a mode of the imaging system 50 wherein an image is being generated by the emission of the localization radiopharmaceutical, but the imaging system 50 is not acquiring data. For example, the persistence mode generates an image from emission data acquired currently or over the previous one or two seconds, thereby generating a lower resolution image. In the persistence mode, a larger amount of statistical emission data is generally not acquired and processed, such as in an NM image study.

Accordingly, in various embodiments, the localization radiopharmaceutical may be used to localize and position the ROI 66 within the FOV of the detectors 54 using the display 72 as a virtual view finder. It should be noted that in the persistence phase of imaging the imaging system 50 is set to cover an energy range, namely to define an energy window for detection by the detectors 54, that is based on or optimized for the localization radiopharmaceutical.

Once the ROI 66 is positioned within the FOV of the detectors 54, imaging of the patient 58 is initiated. In particular, and referring to the method 30, an imaging scan of the ROI 66 is initiated at 40. For example, an imaging mode is initiated with the patient 58 still positioned such that the ROI 66 is within the FOV of the detectors 54. Accordingly, the patient 58, once positioned using image information acquired using the localization radiopharmaceutical, is not moved. Thus, after the persistence phase and positioning of the patient, a dynamic acquisition is started wherein image data may be acquired, for example, photon counts from the radiopharmaceutical decay.

After the imaging scan is initiated, another radiopharmaceutical is administered to the patient 58, such as an isotope for use in the dynamic image acquisition. The radiopharmaceutical for imaging is different than the localization radiopharmaceutical. As described in more detail herein, the localization radiopharmaceutical was previously selected such that the energy peaks of the localization radiopharmaceutical do not impact the dynamic study, for example, do not create cross-talk with the radiopharmaceutical used for the dynamic study. For example, the localization radiopharmaceutical may be Thallium-201, having an energy peak at about 70 keV, and the dynamic imaging radiopharmaceutical may be Technetium-99m having an energy peak at about 140 keV. Thus, the energy peak and energy window of Thallium-201 is lower than that of Technetium-99m. However, it should be noted that the localization radiopharmaceutical may have a higher energy peak and energy window than the dynamic imaging radiopharmaceutical. In some embodiments, a portion of the energy windows of the localization radiopharmaceutical and the dynamic imaging radiopharmaceutical may overlap.

Additionally, different types of radiopharmaceuticals formed from different isotopes may be used.

It should be noted that the radionuclide introduced into the patient 58 as the localization radiopharmaceutical or the dynamic imaging radiopharmaceutical may be chemically bound to a complex that acts characteristically within the patient 58, which is commonly referred to as a tracer. In the presence of disease, a tracer will often be distributed around the body of the patient 58 and/or processed differently. Concentration of the tracer is then representative of increased physiological function shown as hot-spots on displayed images of the radio-accumulation.

As with the localization radiopharmaceutical, the dynamic imaging radiopharmaceutical uptakes and is localized within the ROI 66, for example, the organ of interest, such as the heart. Thereafter, image data is acquired at 44 for the ROI 66 that has been positioned within the FOV of the imaging detectors 54. For example, in a dynamic study, the dynamic acquisition records the dynamic process of the radiopharmaceutical uptake and redistribution in the ROI 66, such as the organ to be imaged. For example, the image information may include emitted photon count information used to reconstruct an image, which may form a cine loop showing the dynamic acquisition with a plurality of NM images over time. The NM images are reconstructed and may be displayed at 46 as one or more images of the ROI 66. The NM images may be displayed, for example, on the display 72 of the imaging system 50 (shown in FIG. 2).

Figure 3:
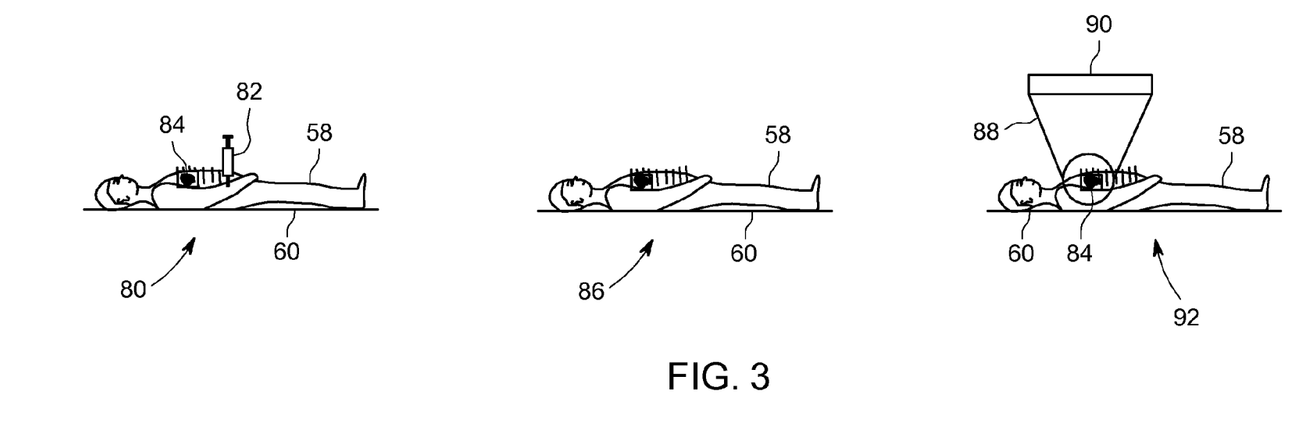
FIG. 3 is a diagram illustrating patient positioning using a localization radiopharmaceutical in accordance with various embodiments.
Figure 4:
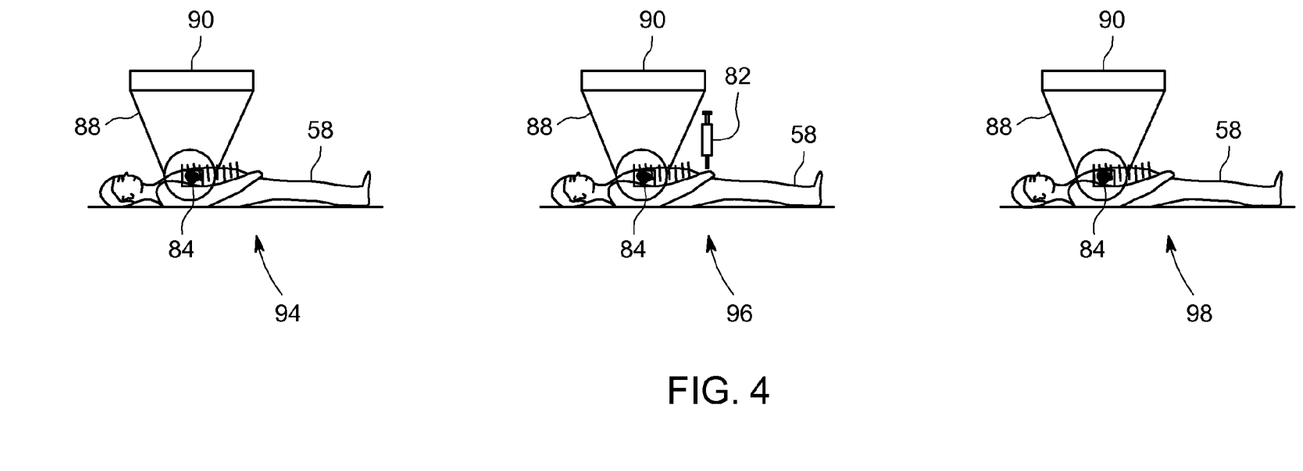
FIG. 4 is diagram illustrating a dynamic NM study performed on a patient positioned within a field of view of an imaging detector in accordance with various embodiments.

Thus, as shown in FIG. 3, a patient 58 may be positioned for a dynamic study as shown in FIG. 4. FIGS. 3 and 4 illustrate a dynamic cardiac study. In particular, at 80, a localization radiopharmaceutical is administered to the patient 56, for example, intravenously using an injection system 82, represented by a needle in FIGS. 3 and 4. The region of interest in the dynamic study is a heart 84 of the patient 56. Accordingly, the localization radiopharmaceutical is produced to uptake into the heart 84. Thus, once the localization radiopharmaceutical is administered, the localization radiopharmaceutical uptakes into and is localized within the heart 84. Thereafter, the heart 84 is positioned within a FOV 88 of a gamma camera 90 at 92. For example, the gamma camera 90 may be collimated to have a focused or small FOV that is directed towards the heart 84. Accordingly, in some embodiments, using persistence images of the heart 84 generated from the decay of the localization radiopharmaceutical, the patient 58 is positioned (e.g., using the patient bed 60) such that the heart 84 is within the FOV 88 of the gamma camera 90.

Thereafter, with the patient 58 positioned in the FOV 88 of the gamma camera 90, a dynamic scan is initiated at 94. For example, a dynamic NM scan or study may be initiated with a dynamic imaging radiopharmaceutical administered thereafter at 96, for example, using the injection system 82. Dynamic image data may then be acquired at 98, which shows the dynamic radiopharmaceutical uptake into the heart 84, which is already positioned inside or within in the FOV 88 of the gamma camera 90.

Figure 5:
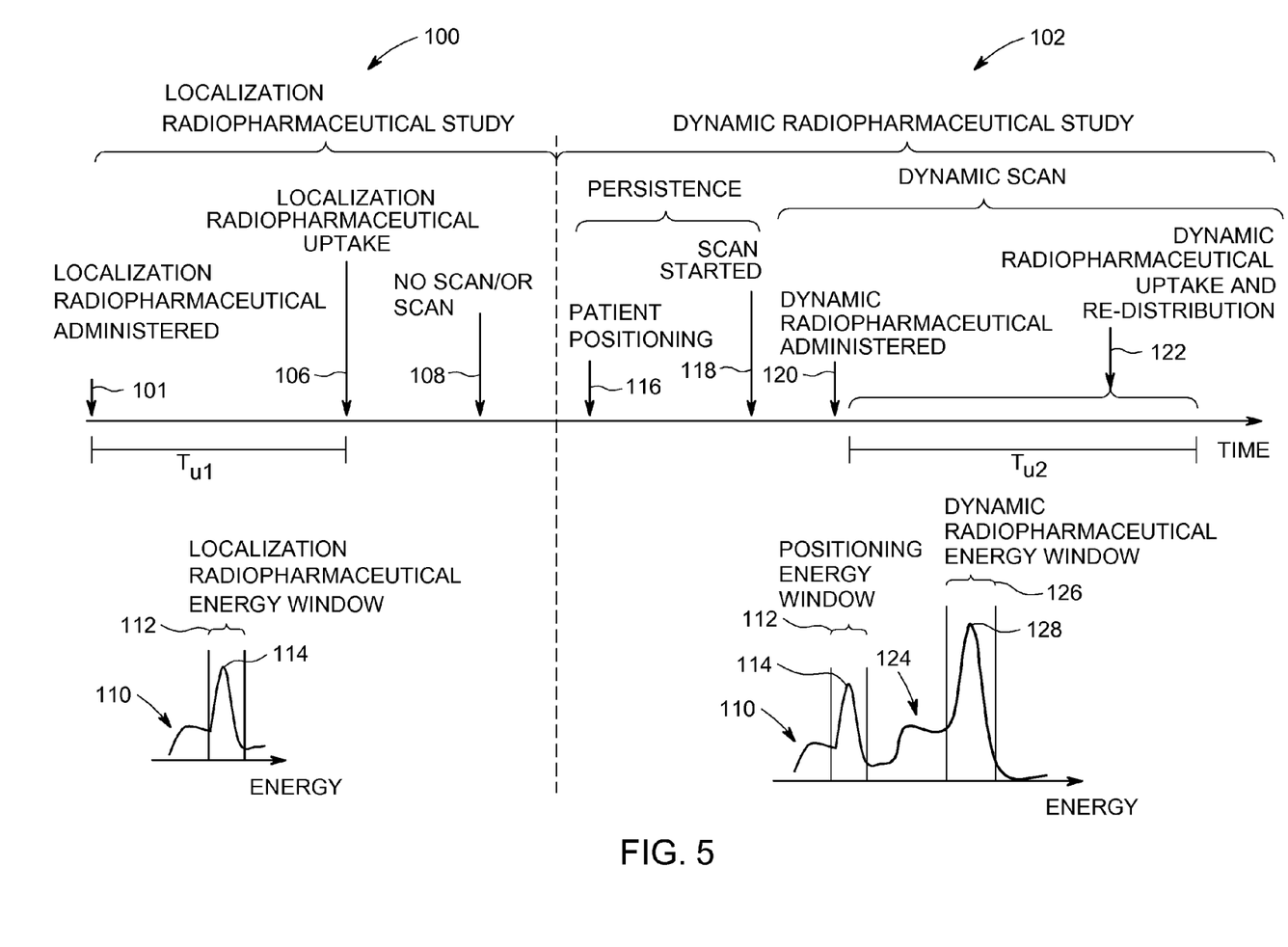
FIG. 5 is a diagram illustrating timing of a localization radiopharmaceutical study and a dynamic radiopharmaceutical study performed in accordance with various embodiments.

An exemplary timeline of a dynamic study performed in accordance with various embodiments is shown in FIG. 5. In particular, a localization radiopharmaceutical study 100 is performed to position an ROI of a patient within a FOV of a gamma camera, followed by a dynamic radiopharmaceutical study 102. In particular, the radiopharmaceutical study 100 includes administering a localization radiopharmaceutical at 104, waiting a time $T_{u1}$ for the localization radiopharmaceutical to uptake at 106, which may include at 108 no scanning or scanning (such as to perform a tissue viability study). The localization radiopharmaceutical study 100 includes using a localization radiopharmaceutical with an isotope having an energy profile 110 with an energy window 112 and an energy peak 114.

After performing the localization radiopharmaceutical study 100, and in particular, the dynamic radiopharmaceutical study 102, at 116 the patient is positioned within the FOV of the gamma camera using persistence imaging based on the localization of the localization radiopharmaceutical. It should be noted that the positioning of the patient using the localization radiopharmaceutical may be performed as part of the localization radiopharmaceutical study 100. Once the patient is positioned, and in particular, the ROI (e.g., heart) of the patient is positioned within the FOV of the gamma camera using the persistence image of the ROI, the dynamic imaging is initiated, and in particular, the dynamic scan is started at 118. Thereafter, a dynamic imaging radiopharmaceutical is administered at 120 with the patient still in the same position such that the ROI is within the FOV of the gamma camera prior to administration of the dynamic imaging radiopharmaceutical. Thereafter, at 122 during time $T_{u2}$, the dynamic imaging radiopharmaceutical uptakes and redistributes to the ROI, which uptake and redistribution is scanned with the gamma camera as the ROI is already positioned within the FOV of the gamma camera.

The dynamic radiopharmaceutical study 102 includes using a dynamic imaging radiopharmaceutical with an isotope having an energy profile 124 with an energy window 126 and an energy peak 128. As can be seen, there is no overlap between the energy window 112 and an energy peak 114 of the energy profile 110 for the localization radiopharmaceutical and the energy window 126 and an energy peak 128, respectively, of the energy profile 124 of the dynamic imaging radiopharmaceutical.

Thus, various embodiments provide patient positioning during a persistence imaging phase prior to administering a radiopharmaceutical intended for dynamic study using a different radiopharmaceutical. The localization radiopharmaceutical is administered to patient, then the imaging organ uptakes the localization radiopharmaceutical prior to the dynamic study starting. The persistence phase of imaging is implemented using the localization radiopharmaceutical, which has energy peaks non-overlapping with the main energy peaks of the radiopharmaceutical used for the dynamic study. Thus, the patient, and in particular the ROI of the patient, is positioned with the FOV of the gamma camera, which may have a small FOV, prior to administration of the radiopharmaceutical for the dynamic study.

Accordingly, the various embodiments may operate as an enabler for dynamic imaging in small FOV gamma cameras, for example, as a cardiac, brain, kidney and other dynamic application enabler in small FOV gamma cameras. As another example, the various embodiments may operate as an enabler for Tl-201 viability—Tc99m Sestamibi, Tl-201 viability—Tc99m Teboroxime blood flow in small FOV cardiac gamma cameras.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for nuclear medicine (NM) imaging, the method comprising:
   generating images of a region of interest (ROI) from radioactive emissions from a localization radiopharmaceutical to position the ROI in a field-of-view (FOV) of a gamma camera based on the generated images of the ROI; and
   performing an imaging scan of the ROI, after positioning of the ROI in the FOV of the gamma camera, using an imaging radiopharmaceutical to acquire image data of the ROI, wherein the imaging radiopharmaceutical is different than the localization radiopharmaceutical and the images of the ROI for positioning the ROI in the FOV of the gamma camera are generated from radioactive emissions acquired from the localization radiopharmaceutical at a different time than radioactive emissions acquired from the imaging radiopharmaceutical during the imaging scan.

2. A method in accordance with claim 1 further comprising imaging the ROI using a persistence mode to locate the ROI for positioning in the FOV of the gamma camera.

3. A method in accordance with claim 1 wherein the localization radiopharmaceutical and the imaging radiopharmaceutical have non-overlapping energy peaks.

4. A method in accordance with claim 1 wherein the localization radiopharmaceutical and the imaging radiopharmaceutical have non-overlapping energy windows.

5. A method in accordance with claim 1 wherein the localization radiopharmaceutical has an energy peak and an energy window less than the energy peak and energy window of the imaging radiopharmaceutical.

6. A method in accordance with claim 1 further comprising performing an NM scan using the localization radiopharmaceutical.

7. A method in accordance with claim 6 wherein the NM scan comprises a tissue viability scan.

8. A method in accordance with claim 1 wherein an administered dose of the localization radiopharmaceutical is less than an administered dose of the imaging radiopharmaceutical.

9. A method in accordance with claim 1 wherein the imaging scan comprises a dynamic NM study.

10. A method in accordance with claim 9 wherein the NM study comprises a dynamic uptake and redistribution study.

11. A method is accordance with claim 1 wherein the gamma camera comprises a collimated gamma detector having a focused FOV.

12. A method is accordance with claim 1 wherein the gamma camera comprises a collimated gamma detector having a focused and reduced FOV.

13. A method in accordance with claim 1 wherein the ROI is within a patient and the imaging radiopharmaceutical is administered to the patient after positioning of the ROI within the FOV of the gamma camera and after initiating an imaging scan for a dynamic study, the imaging scan subsequent to a persistence scan performed to acquire the images for the ROI from the radioactive emissions from the localization radiopharmaceutical.

14. A method in accordance with claim 1 wherein the localization radiopharmaceutical and the imaging radiopharmaceutical are both configured to uptake into a same ROI.

15. A method in accordance with claim 1 wherein the localization radiopharmaceutical is Thallium-201 and the imaging radiopharmaceutical is Technetium-99 m.

16. A method in accordance with claim 1 wherein the radioactive emissions from the localization radiopharmaceutical are acquired only during a first time period and the radioactive emissions from the imaging radiopharmaceutical are acquired only during a second time period, wherein the first and second time periods are non-overlapping and the first time period is before the second time period.

17. A method in accordance with claim 1 wherein generating images of the ROI comprises generating persistence images having a lower resolution than images generated during the imaging scan and not providing diagnostic image data.

18. A method in accordance with claim 1 wherein the gamma camera remains stationary after positioning of the ROI in the FOV of the gamma camera and during the imaging scan.

19. A method for nuclear medicine (NM) imaging, the method comprising:
 performing a localization radiopharmaceutical study using a localization radiopharmaceutical to position a region of interest (ROI) of a patient in a field-of-view (FOV) of a gamma camera; and
 performing, after the localization radiopharmaceutical study, a dynamic radiopharmaceutical study using a dynamic radiopharmaceutical to acquire radiopharmaceutical uptake and redistribution information for the ROI, wherein the localization radiopharmaceutical is different than the dynamic radiopharmaceutical and radioactive emissions from the localization radiopharmaceutical are acquired by the gamma camera at a different time than radioactive emissions from the dynamic radiopharmaceutical.

20. A method in accordance with claim 19 wherein the localization radiopharmaceutical and the dynamic radiopharmaceutical have energy profiles with non-overlapping energy peaks.

21. A method in accordance with claim 19 wherein the localization radiopharmaceutical and the dynamic radiopharmaceutical have energy profiles with non-overlapping energy windows.

22. A method in accordance with claim 19 wherein the localization radiopharmaceutical has a lower energy peak than an energy peak of the dynamic radiopharmaceutical.

23. A method in accordance with claim 19 further comprising using persistence imaging to position the ROI of the patient in the FOV.

24. A method in accordance with claim 19 further comprising acquiring NM data during the localization radiopharmaceutical study.

25. A method in accordance with claim 19 wherein the gamma camera comprises a focused and reduced FOV gamma camera and further comprising positioning the ROI of the patient in a FOV of the focused and reduced FOV gamma camera using the localization radiopharmaceutical study.

26. A nuclear medicine (NM) imaging system comprising:
 an NM imaging scanner having at least one imaging detector;
 a patient table supporting a patient thereon and positionable within the NM imaging scanner; and
 a processor configured to acquire images of a region of interest (ROI) of the patient based on radioactive emissions from a localization radiopharmaceutical administered to the patient, the patient positioned with the FOV of the gamma camera based on the acquired images, and the processor further configured to acquire dynamic NM image data of the positioned patient using an imaging radiopharmaceutical, wherein the localization radiopharmaceutical is different than the imaging radiopharmaceutical and the images of the ROI for positioning the ROI in the FOV of the gamma camera are generated from radioactive emissions acquired from the localization radiopharmaceutical at a different time than radioactive emissions acquired from the imaging radiopharmaceutical during the imaging scan.

* * * * *